(12) United States Patent
Petersen et al.

(10) Patent No.: US 11,911,569 B2
(45) Date of Patent: Feb. 27, 2024

(54) IMMERSIVE DISTRACTION THERAPY

(71) Applicant: BioVentures, LLC, Little Rock, AR (US)

(72) Inventors: Erika Petersen, Little Rock, AR (US); Mohamed Abdeldayem, Little Rock, AR (US); Adria Abella Villafranca, Little Rock, AR (US); Kevin Sexton, Little Rock, AR (US); Joseph Sanford, Little Rock, AR (US)

(73) Assignee: BIOVENTURES, LLC, Little Rock, AR (US)

( * ) Notice: Subject to any disclaimer, the term of this patent is extended or adjusted under 35 U.S.C. 154(b) by 206 days.

(21) Appl. No.: 17/389,908

(22) Filed: Jul. 30, 2021

(65) Prior Publication Data
US 2022/0031997 A1 Feb. 3, 2022

Related U.S. Application Data (60) Provisional application No. 63/059,849, filed on Jul. 31, 2020.

(51) Int. Cl.
*A61M 21/00* (2006.01)
*G06F 3/01* (2006.01)
*A61F 5/37* (2006.01)

(52) U.S. Cl.
CPC ............... *A61M 21/00* (2013.01); *A61F 5/37* (2013.01); *G06F 3/011* (2013.01); *A61M 2021/005* (2013.01); *A61M 2021/0022* (2013.01); *A61M 2021/0027* (2013.01)

(58) Field of Classification Search
CPC ...... A61B 90/10–18; A61F 5/37–3707; A61M 2205/507; G06F 3/011; H04N 13/332–346
See application file for complete search history.

(56) References Cited

U.S. PATENT DOCUMENTS

| | | | |
|---|---|---|---|
| D701,206 S | 3/2014 | Lucky et al. | |
| D792,398 S | 7/2017 | Costa et al. | |
| 2008/0086063 A1* | 4/2008 | Baxter | A61M 5/422 601/46 |
| 2017/0340297 A1* | 11/2017 | Varkuti | G16H 40/63 |
| 2018/0239416 A1* | 8/2018 | Laskin | G06F 3/011 |
| 2019/0175284 A1* | 6/2019 | Herbelin | A61B 90/10 |
| 2020/0008687 A1* | 1/2020 | Friedlander | A61B 5/064 |
| 2021/0077333 A1* | 3/2021 | Kumar | A61G 15/125 |
| 2021/0299434 A1* | 9/2021 | Månsson | A61N 1/0476 |

\* cited by examiner

*Primary Examiner* — Thaddeus B Cox
(74) *Attorney, Agent, or Firm* — POLSINELLI PC (57) ABSTRACT

Disclosed herein is an immersive distraction apparatus including an attachment portion including an engagement element and a front plate having two cut outs fitting lenses therein and a base portion coupled with the attachment portion having a display aperture sized to receive a device. The immersive distraction apparatus mountable on a surgical head frame using one or more connectors such that an immersive distraction therapy can be provided to a patient undergoing surgery via a virtual reality environment.

14 Claims, 12 Drawing Sheets

IMMERSIVE DISTRACTION THERAPY

CROSS-REFERENCE TO RELATED APPLICATIONS

This application claims priority to U.S. Provisional Application No. 63/059,849, filed Jul. 31, 2020, the contents of which are entirely incorporated by reference herein.

FIELD

The present disclosure relates to a surgical equipment with visual stimulation and methods of use thereof.

BACKGROUND

Certain surgical procedures are required to be performed while a patient is awake and alert. Such surgical procedures are typically used to treat neurological conditions and can require the patient to interact with doctors at various points throughout the procedure. While portions of the surgical procedures can be performed while the patient is under anesthesia, patients can still experience anxiety during the portions of the procedures for which they are awake. Such anxiety can make it difficult for the patient to focus on tasks the surgeon requests the patient perform.

Therefore, there is a need for an immersive distraction therapy which can desensitize the patient to their stressful surroundings during a medical procedure while still allowing them to perform tasks provided to them.

SUMMARY

This disclosure provides an immersive distraction apparatus that can be used in immersive distraction therapies during stressful surgical procedures. The immersive distraction apparatus can include a base portion having a display aperture and a viewing frame that can be coupled with a head frame used in neurosurgeries. The immersive distraction apparatus also includes an attachment portion coupled with the base portion, the attachment portion including lenses through which patients can view a device disposed in the display aperture of the base portion, the device providing an immersive distraction therapy. The device can also include an auditory component. The distraction component of the device includes Bluetooth, wired, wifi, or other known connectivity to the virtual reality system, which aids to minimize environmental noise. In an exemplary embodiment the apparatus includes a bone anchored conduction of sound to enhance the distraction experience. In some embodiments, the apparatus uses the frame connector vibratory tactile stimuli which aids to enhance distraction.

In some aspects, the immersive distraction apparatus can be used during surgical procedures where the patient is required to be awake. During the surgery, the immersive distraction apparatus can be used with a device having software which can be used to create a particular environment for the patient. The software environments can be used to track patient brain and motor function or entertain the patient to reduce anxiety which occurs during brain surgery where the patient is awake.

Further disclosed herein is an immersive distraction therapy system. The system may include an immersive distraction apparatus and a head frame. In some aspects, the immersive distraction apparatus may include an attachment portion comprising an engagement element and a front plate; and a base portion coupled with the attachment portion, the base portion comprising a top panel and a display aperture formed between a viewing frame and a back plate, the top panel having a slot formed therein to retain the engagement element of the attachment portion. In additional aspects, the head frame may include at least two supports, where the immersive distraction apparatus is mounted to the at least two supports. In various aspects, the immersive distraction system may further include a patient table, an arc system attached to a patient table to provide locations of target coordinates, one or more MR accessories, and/or one or more CT accessories.

Also disclosed herein is a method for using an immersive distraction therapy during procedures in which the patient is required to perform various tasks. The method may include placing a device configured to request specific tasks from a patient in an immersive distraction device to encourage the patient to complete a series of tasks during surgical procedures.

BRIEF DESCRIPTION OF THE DRAWINGS

The description will be more fully understood with reference to the following figures and data graphs, which are presented as various embodiments of the disclosure and should not be construed as a complete recitation of the scope of the disclosure. It is noted that, for purposes of illustrative clarity, certain elements in various drawings may not be drawn to scale. Understanding that these drawings depict only exemplary embodiments of the disclosure and are not therefore to be considered to be limiting of its scope, the principles herein are described and explained with additional specificity and detail through the use of the accompanying drawings in which.

Reference characters indicate corresponding elements among the views of the drawings. The headings used in the figures do not limit the scope of the claims.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment", "an embodiment", or "an aspect" means that a particular feature, structure, or characteristic described in connection with the embodiment is included in at least one embodiment of the disclosure. The appearances of the phrase "in one embodiment" or "in one aspect" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Provided herein is an immersive distraction apparatus couplable with a surgical head frame methods of use thereof to reduce anxiety of patients. As described above, there are various surgical procedures including, but not limited to, neurological procedures during which a patient must remain awake and interact with a surgeon. Head frames, such as stereotactic head frames, can be used to stabilize a patient's head during neurosurgical procedures including implantation of deep brain stimulators, depth electrodes, stereotactic brain biopsies, and cranial radiosurgeries. The immersive distraction apparatus described herein can be coupled with such headframes in order to provide an immersive distraction therapy. In at least one instance, the present immersive distraction apparatus can include a display aperture in which a device can be inserted to provide a patient with an immersive experience during a surgical procedure.

Figure 1:
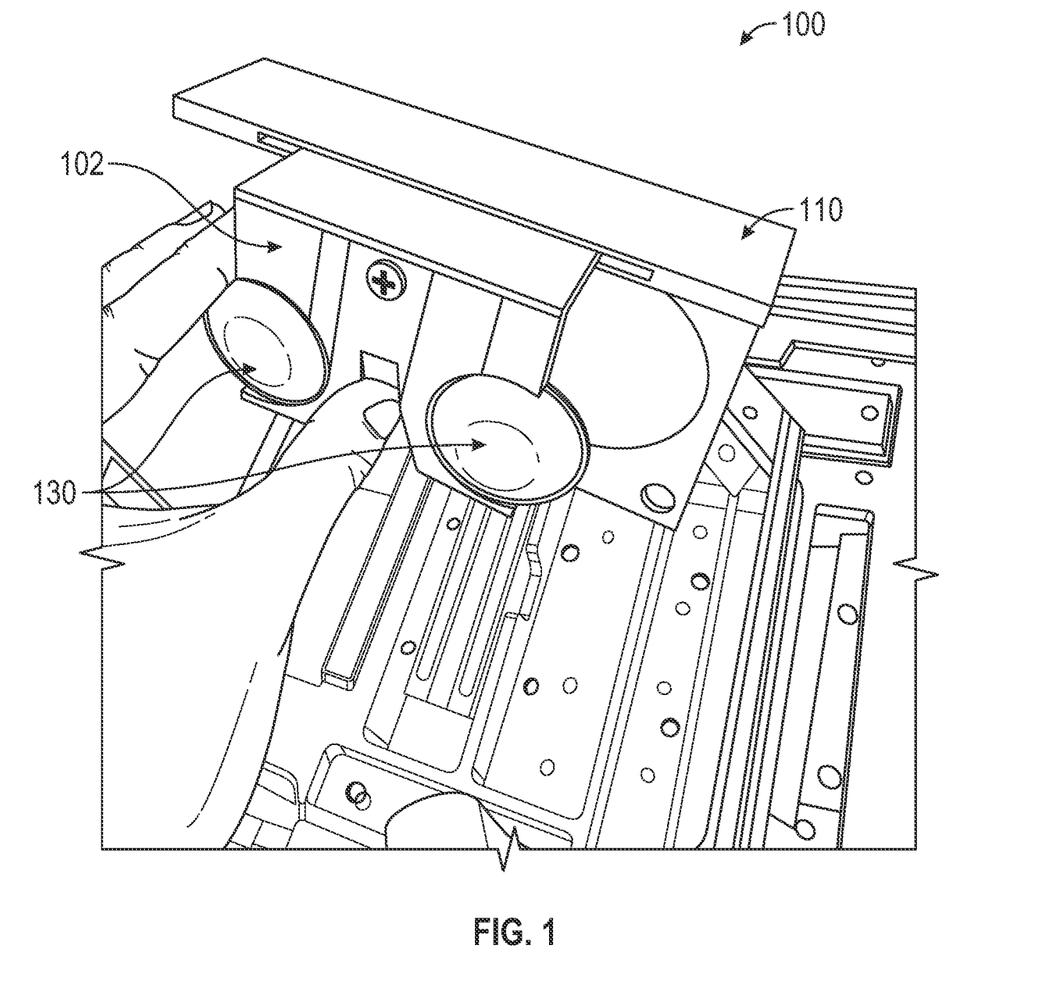
FIG. 1 is an example immersive distraction apparatus in accordance with the therapies described herein.

FIG. 1 illustrates an immersive distraction apparatus 100 having an attachment portion 102 and a base portion 110. The attachment portion 102 of the immersive distraction apparatus 100 can be coupled with the base portion 110 using any suitable means. The immersive distraction apparatus 100 can further include two lenses 130 coupled with the attachment portion 102. A detailed view of the attachment portion 102 is provided in FIGS. 2A and 2B.

Figure 2A:
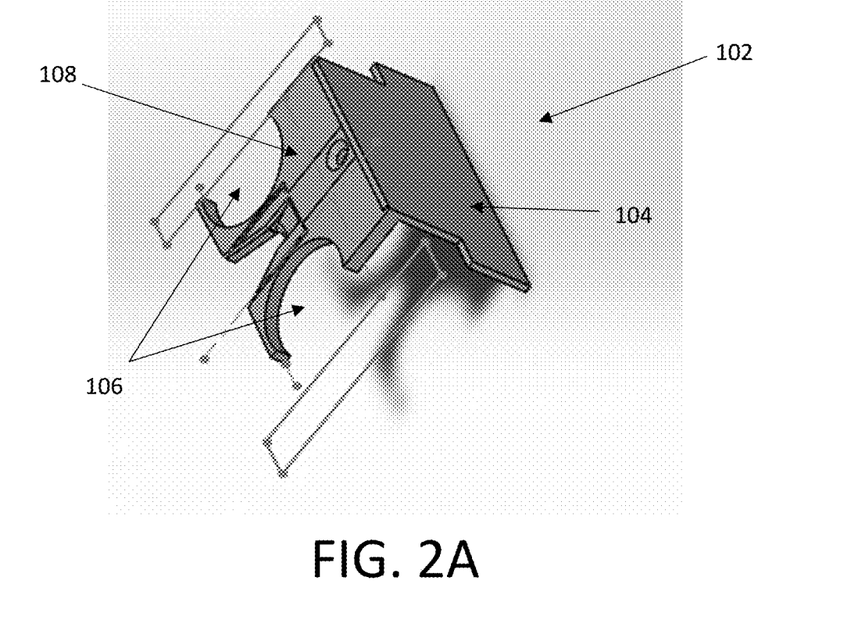
FIG. 2A is a front, perspective view of an attachment portion of a immersive distraction apparatus in accordance with the present disclosure.
Figure 2B:
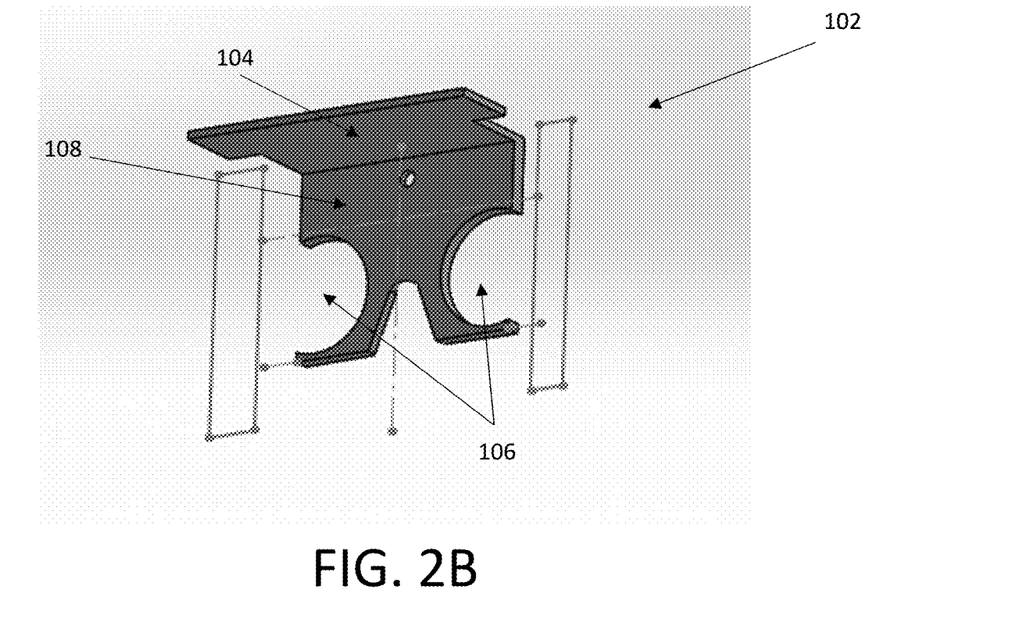
FIG. 2B is a rear, perspective view of the attachment portion of the immersive distraction apparatus of FIG. 2A, in accordance with the present disclosure.

Specifically, FIG. 2A shows a front, perspective view of the attachment portion 102 can include an engagement element 104 which is couplable with the base portion 110 of the immersive distraction device 100. The attachment piece 102 can further include a front plate 108 which includes two cut outs 106. Each of the cut outs 106 can be sized to fit one of the lenses as described above. A rear, perspective view of the attachment portion 102 of the immersive distraction apparatus 100 is shown in FIG. 2B. As indicated, the front plate 108 which holds the lenses 130 is located along the front edge of the engagement element 104, providing a predetermined distance between the lenses 103 and a device which can be used with the immersive distraction apparatus 100. In at least one instance, the attachment portion 102 can be customizable such that the distance between lenses is adjusted based on the patient's pupillary distance. For example, some attachment portions can have a shorter distance between the lenses for use on patients with small faces or pediatric surgery.

Figure 3A:
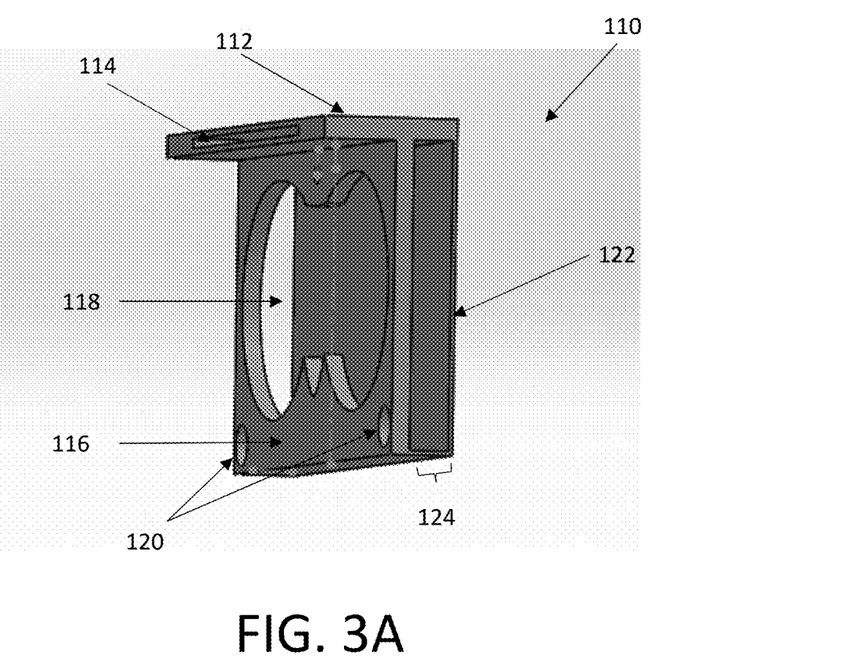
FIG. 3A is a perspective view of a base portion of an immersive distraction apparatus in accordance with the present disclosure.
Figure 3B:
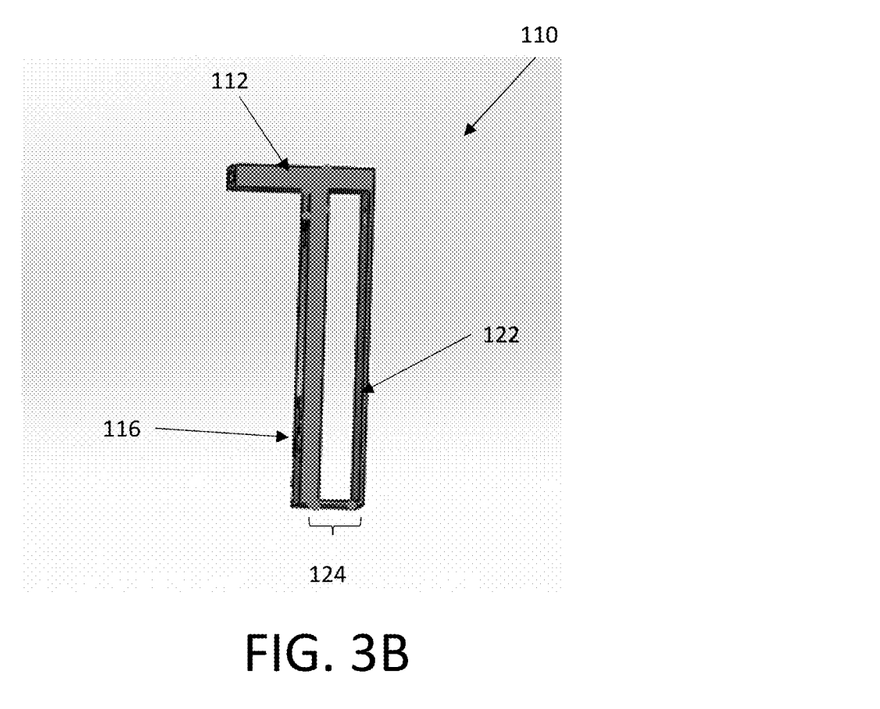
FIG. 3B is a side view of the base portion of the immersive distraction apparatus of FIG. 3A, in accordance with the present disclosure.
Figure 3C:
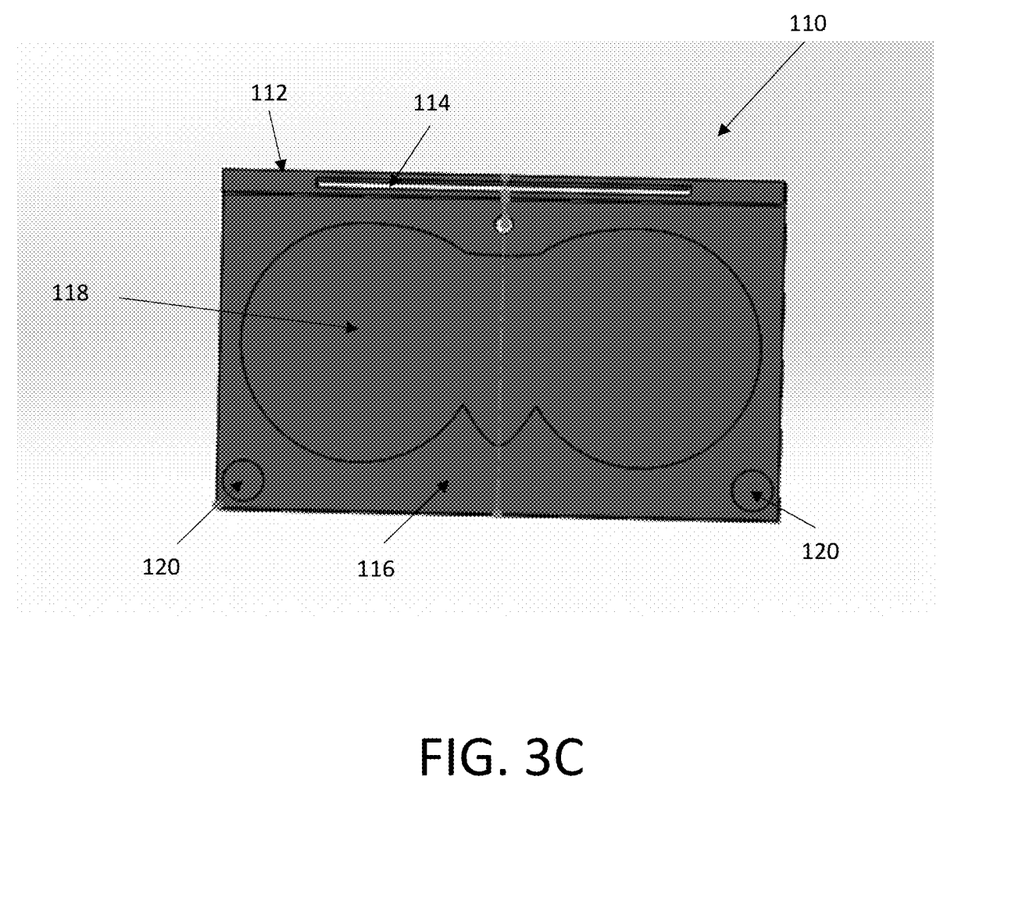
FIG. 3C is an elevational view of the base portion of the immersive distraction apparatus of FIG. 3A, in accordance with the present disclosure.

FIGS. 3A-3C illustrate various views of a base portion 110 of the immersive distraction apparatus 100 as shown in FIG. 1. The base portion 110 can include a top panel 112 having a slot 114. In at least one instance, the slot 114 can engage the engagement element 104 of the attachment portion 102 to secure the attachment portion 102 to the base portion 110. For example, the slot 114 can be sized to fit the engagement element 104 therein. As illustrated in FIGS. 2A and 2B, the engagement element 104 of the attachment portion 102 can include one or more protrusions which can be retained within the top panel 112 of the base portion 110 of the immersive distraction apparatus 100. In an alternative example, the engagement element 104 can be retained within the top panel 112 by any other suitable means.

The attachment portion 102 can further include a viewing frame 116 and a back plate 122 forming a display aperture 124 therebetween, as illustrated in FIGS. 3A and 3B. The display aperture 124 can be sized such that a device can be inserted therein. In at least one instance, the device can be any device having a display including, but not limited to, a personal computing device, a smart phone, a tablet, and the like. In at least one instance, the device can be self-powered, such that no additional cables or wires are required. As illustrated in FIG. 3B, the display aperture 124 can be open at each end to allow for a user to insert the device therein. The viewing frame 116 can include an opening 118, as shown in FIGS. 3A and 3C, which allows a user to see a device inserted into the display aperture 124. The viewing frame 116 of the base portion 110 of the immersive distraction apparatus 100 further includes one or more receiving apertures 120 that can be used to connect the base portion 110 of the immersive distraction apparatus 100 to a head frame during surgical procedures.

The attachment portion 102 may have a focal length controller capable of increasing or decreasing the distance between the lenses and the patient's face. In an embodiment, the focal length controller may be a wheel. In an example, tracks may be located inside of the slot 114 on which the attachment portion 102 may be placed. The wheel may be attached to the attachment portion 102 and connected to the tracks within slot 114 to allow the attachment portion 102 to slide in and out of the slot 114 on the tracks when the wheel is turned, increasing or decreasing the distance between the lenses and the patient's face. In another embodiment, the wheel may be attached to the base portion 110, top panel 112, or any other component of the immersive distraction apparatus 100. In another embodiment, the focal length controller may be a gear mechanism. In other embodiments, the focal length controller may be a slider, an electronic distance translating device, or any other distance translation device known in the art that may be used to adjust the distance between the lenses and the patient's face.

The attachment portion 102 and the base portion 110 of the immersive distraction apparatus 100 can be made of any material suitable to retain a device including, but not limited to, plastic, metal, or any other material that is both structurally sufficient and capable of being sterilized for use in an operating room. In at least one instance, the immersive distraction apparatus 100 can be made of a material that is resistance to bacterial growth. In at least one instance, the attachment portion 102 and the base portion 110 can be three-dimensionally (3D) printed.

Figure 4:
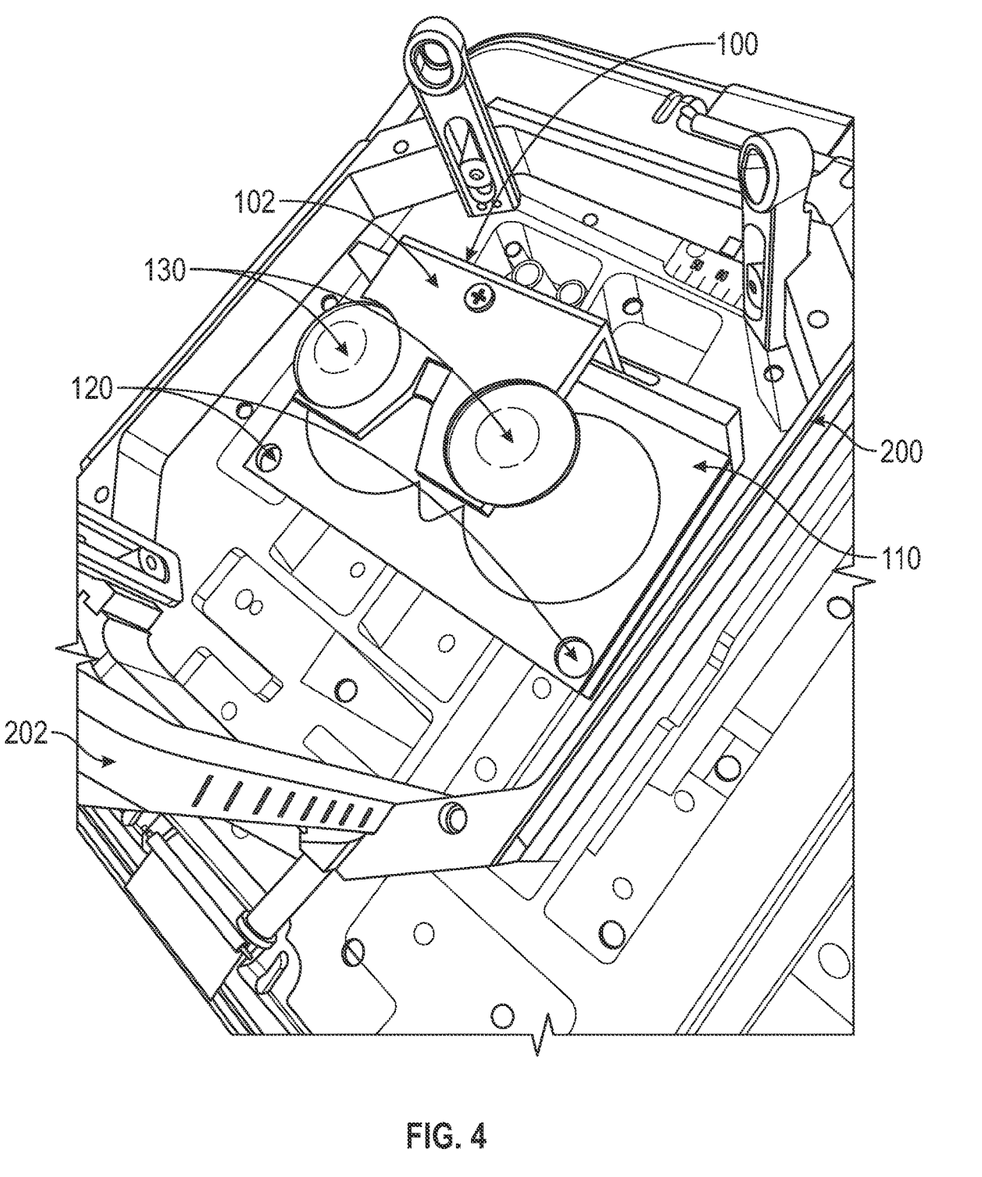
FIG. 4 is an exemplary view of an immersive distraction apparatus and an exemplary head frame which can be used in immersive therapies in accordance with the present disclosure.

FIG. 4 illustrates an assembled view of the immersive distraction apparatus 100 and a head frame 200 which can be used to stabilize a patient's head during neurosurgical procedures. As illustrated, the engagement element 104 of the attachment portion 102 is received in the slot 114 of the base portion 110. The attachment portion 102 and base portion 110 can be sized such that when the attachment portion 102 is secured to the base portion 110 such that lenses 130 coupled with the attachment portion 102 are maintained at an optimal distance from the device.

A head frame 200 as described herein can be any medical head frame used to prevent unwanted movement of a patient's head. In at least one example, during "awake" brain surgeries, a surgeon may need to interact with a patient to ensure certain physical functions are not damaged during the surgery. Having such presence of mind during brain surgery can cause patients to experience extreme levels of anxiety that can distract them or otherwise prevent them from interacting with the surgeon as necessary. The immersive distraction therapies described herein can include a head frame 200 including supports 202 which can be used to mount the immersive distraction apparatus 100 to the head frame 200. Such immersive distraction therapy can be used to distract the patient during surgery to reduce their anxiety. In at least one instance, the immersive distraction therapy can include a virtual reality simulation that is created using the immersive distraction apparatus 100 as a headset through which the patient views the virtual reality.

In an embodiment, the head frame 200 may include at least two, at least three, or four or more supports 202 for mounting the immersive distraction apparatus 100. In some embodiments, the supports 202 may form sides or corners capable of providing space for a patient's head within the head frame. In other embodiments, the head frame 200 may include other shapes and designs capable of supporting the immersive distraction apparatus 100, and/or providing space for a patient's head within the head frame.

Figure 5A:
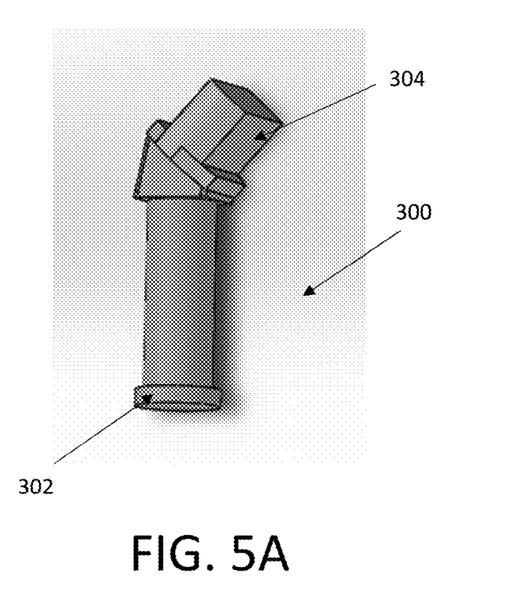
FIGS. 5A-5C illustrate exemplary coupling mechanisms for attaching an immersive distraction apparatus with a head frame in accordance with the present disclosure.
Figure 5B:
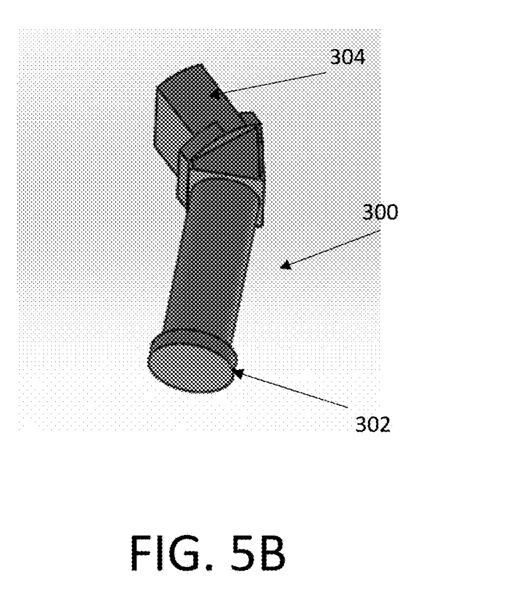
Figure 5C:
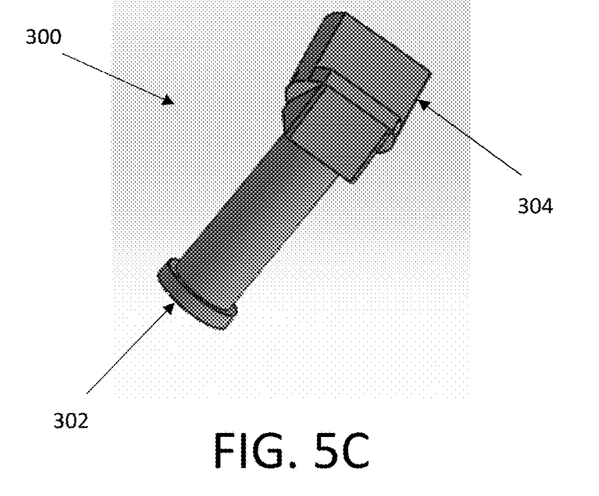

FIGS. 5A-5C illustrate connectors 300 which can be used to mount the immersive distraction apparatus 100 to the supports 202 of the head frame 200. The connectors 300 can include a first projection 302 at one end of the connector 300 and a second projection 304 at the opposite end. The first projection 302 can be received in the receiving apertures 120 of the base portion 110 of the immersive distraction apparatus 100. The first projection 302 can be sized such that once inserted into the receiving aperture 120 the immersive distraction apparatus 100 is secured in the desired position. The second protrusion 304 can be sized to couple an elongated opening 204 in the support 202 of the head frame 200, as illustrated in FIGS. 6A-6B.

Figure 6A:
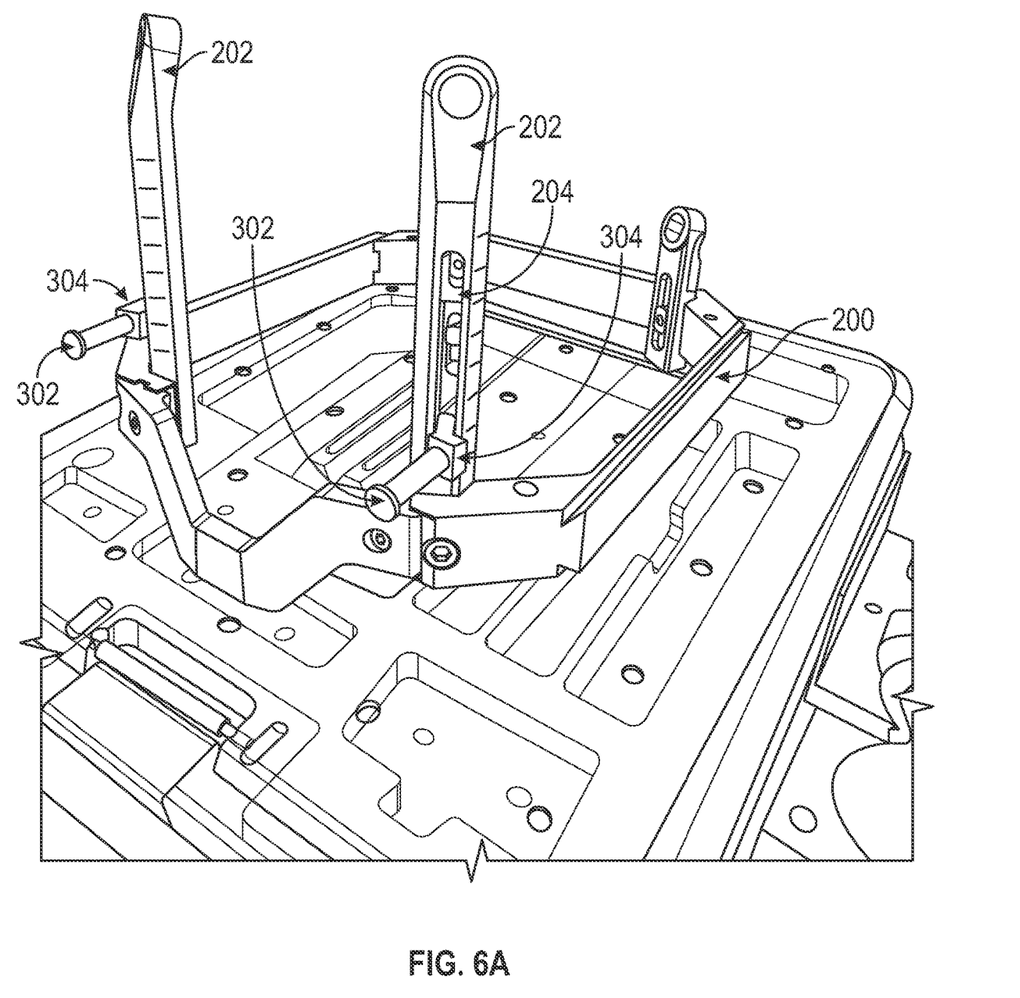
FIGS. 6A and 6B illustrate a head frame having coupling mechanisms attached thereto in accordance with the present disclosure.
Figure 6B:
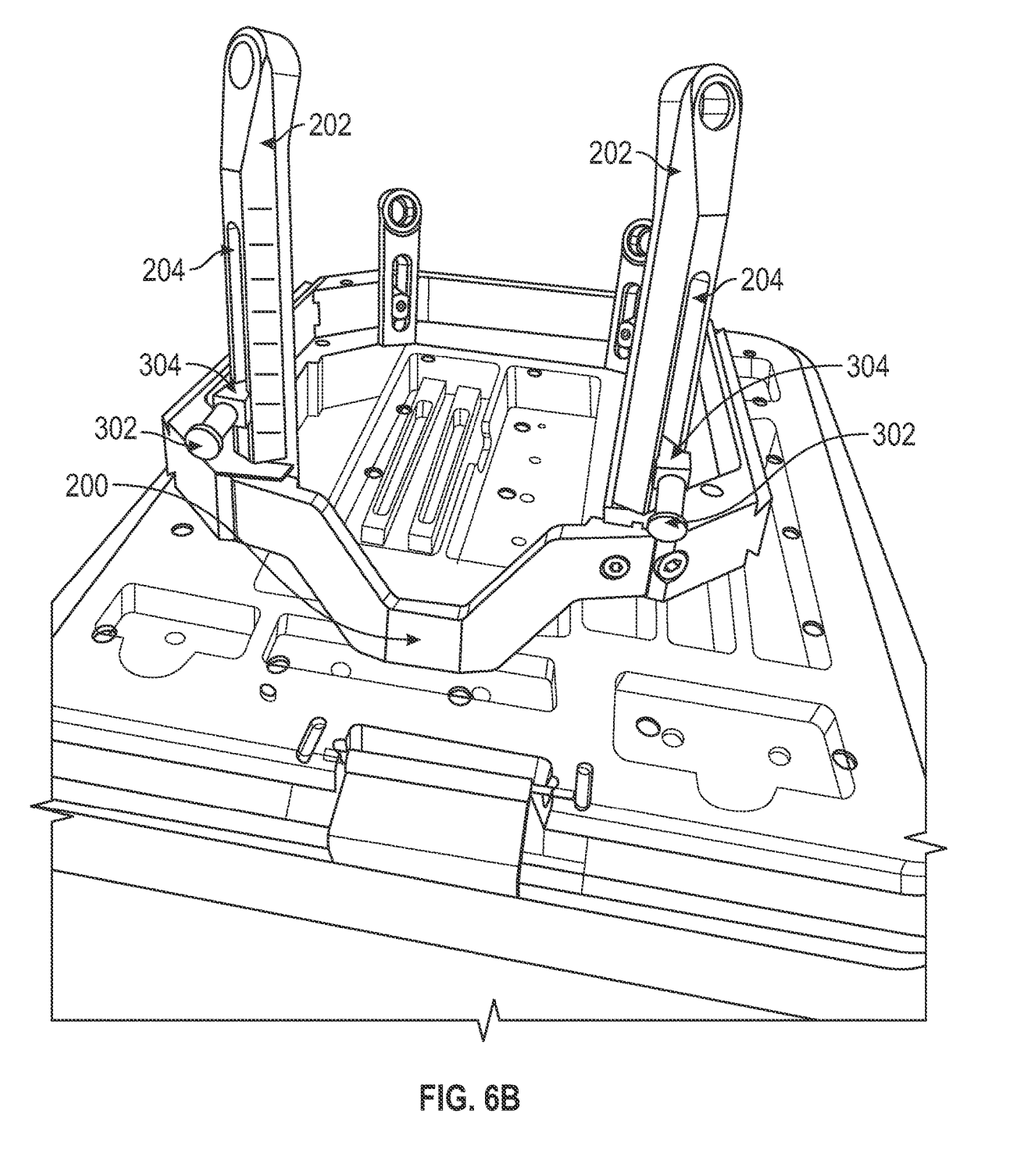

Specifically, FIGS. 6A and 6B show the connectors 300 coupled with supports 202 of the head frame 200. In at least one instance, the second protrusion 304 of the connector 300 can be sized such that it can be moved along the elongated openings 204 of the supports 202. The elongated opening 204 can allow for the adjustment of the height of the immersive distraction apparatus 100 by allowing the connector 300 to be moved along the length of the elongated opening 204. For example, the height of the immersive distraction apparatus 100 can be adjusted to suit each individual patient by moving the connector 300 along the elongated opening 204 so that the lenses 130 are properly aligned with the patient's vision.

In another embodiment, the connectors 300 may be elastic bands made of silicone or other elastic materials operable to provide for connection between the immersive distraction apparatus 100 and one or more of the supports 202 without requiring elongated openings 204 for the connectors 300. In a further embodiment, the connectors 300 may be clipping mechanisms operable to clip to one or more of the supports 202 of the head frame 200 without requiring an elongated opening 204. In a further embodiment, the connectors 300 may be pressure fit mechanisms operable to fit to one or more of the supports 202 of the headframe 200. In other embodiments, other known connection methods may be used to mount the immersive distraction apparatus 100 to the head frame 200.

Figure 7:
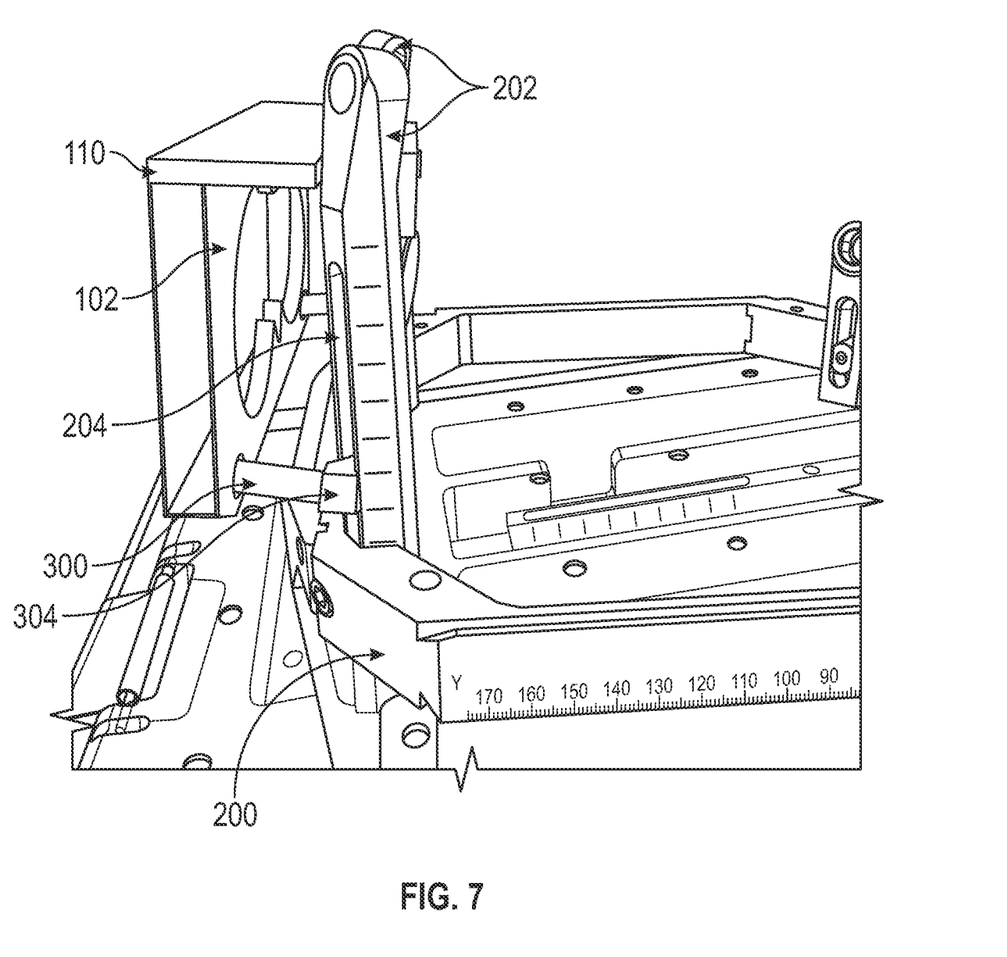
FIG. 7 illustrates a side view of an immersive distraction apparatus coupled with a head frame in accordance with the present disclosure.

FIG. 7 shows the immersive distraction apparatus 100 mounted on the head frame 200 via connectors 300. As illustrated, the first protrusion 302 of each connector is received within the receiving apertures 102 of the base portion 110 and the second protrusion 304 of each connector 300 is received in the elongated slot 204 of the support 202. In at least one instance, the top panel 112 of the base portion 110 of the immersive distraction apparatus 100 can rest against the supports to provide a stable structure.

Figure 8A:
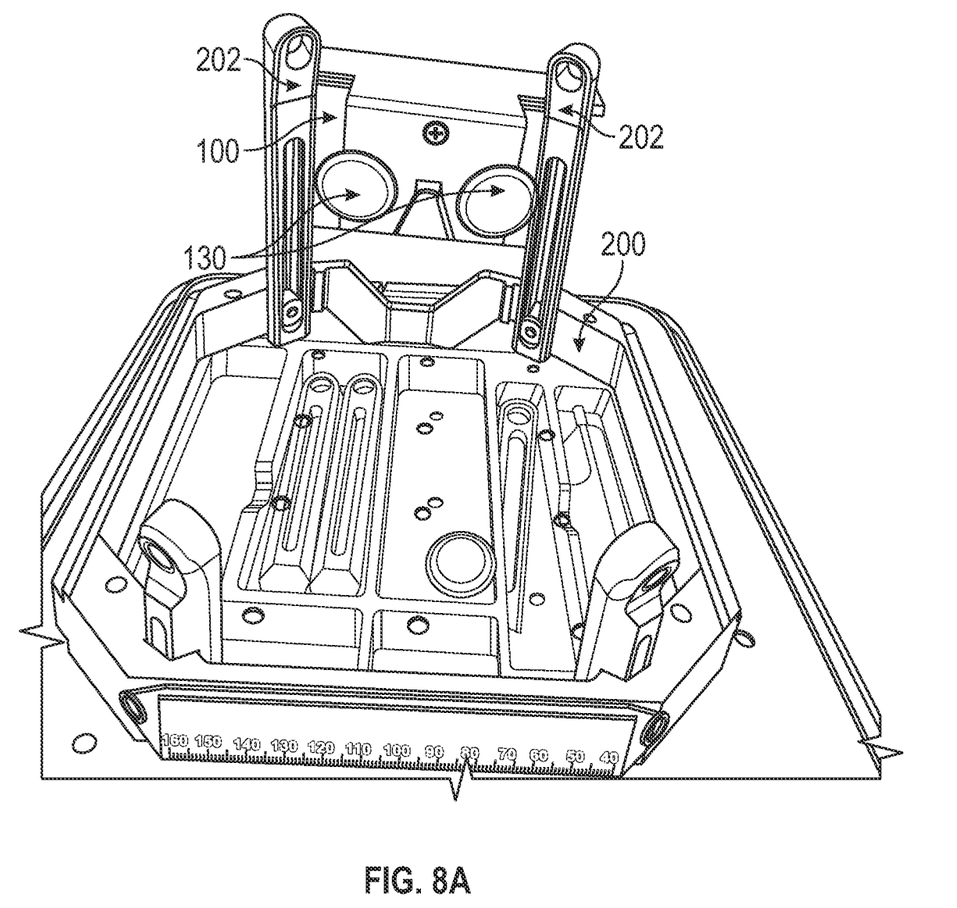
FIGS. 8A and 8B illustrate rear views of an immersive distraction apparatus coupled with a head frame in accordance with the present disclosure.
Figure 8B:
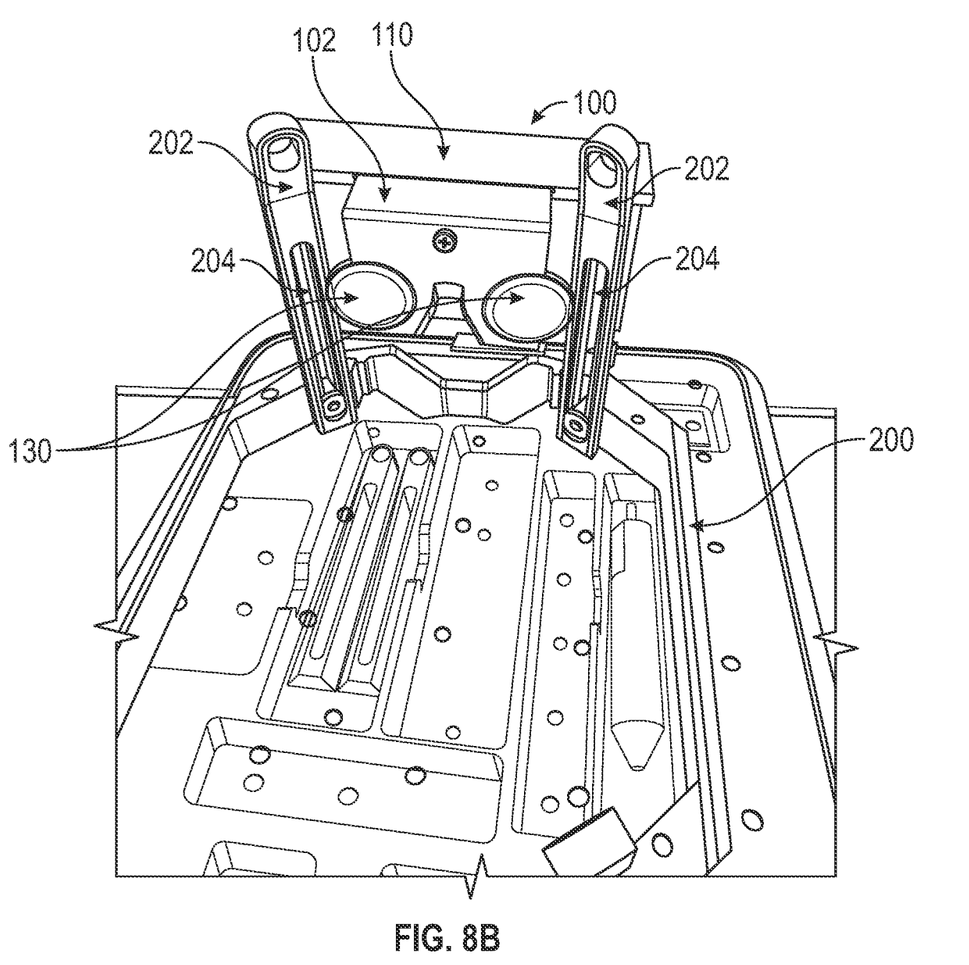
Figure 9:
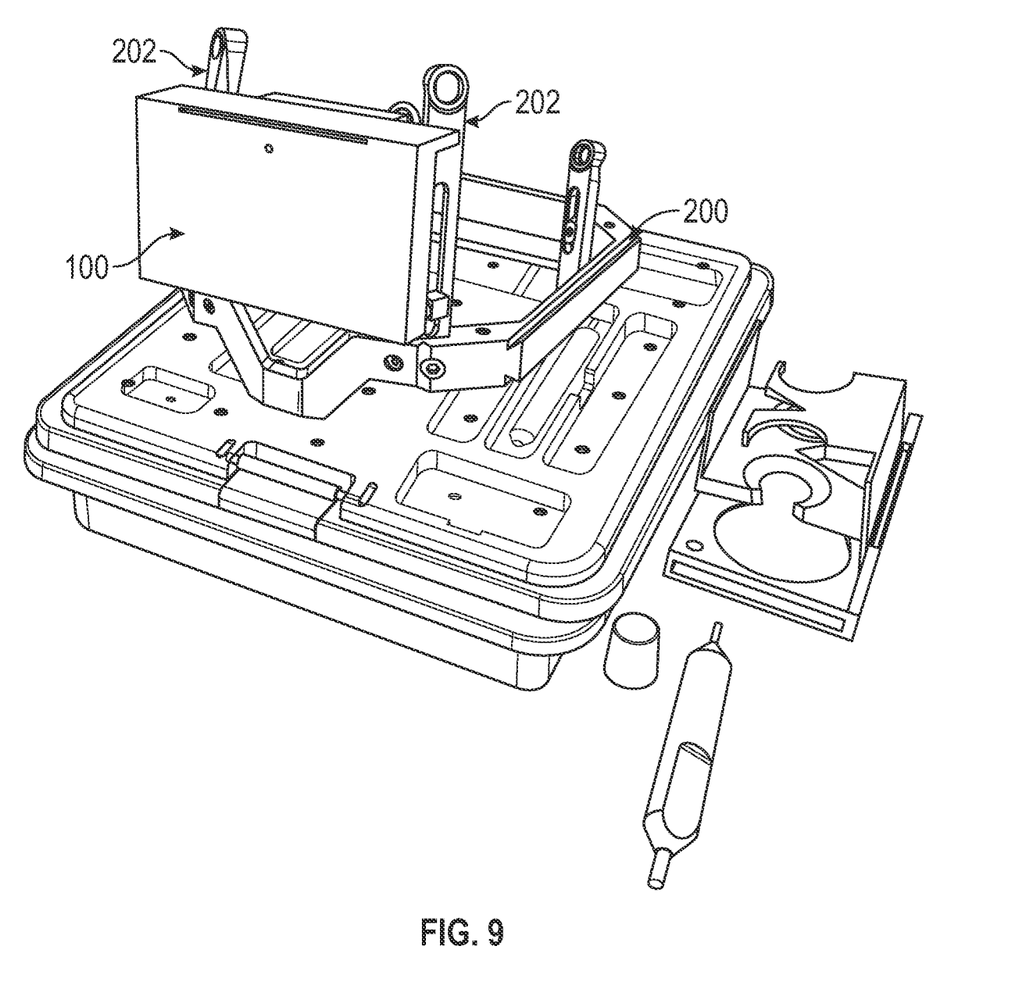
FIG. 9 is a front view of an immersive distraction apparatus coupled with a head frame in accordance with the present disclosure.

FIGS. 8A and 8B illustrate a rear views of the immersive distraction apparatus 100 on the head frame 200. The head frame 200 can be any standard medical head frame 200 including, but not limited to a stereotactic head frame. As shown, lenses 130 can be mounted in the attachment portion 102 of the immersive distraction apparatus 100 such that they are positioned between the patient's head and the display aperture 124 of the base portion 110. The lenses 130 can be permanently or releasably mounted on the attachment portion 102 of the immersive distraction apparatus 100 using any coupling means. In at least one instance, the lenses 130 can be pressure mounted in the cut outs 106. FIG. 9 illustrates a rear view of the immersive distraction apparatus 100 mounted on the supports 202 of the head frame 200.

A system for immersive distraction therapy may also be beneficial. The system may include the immersive distraction apparatus 100 mounted to the head frame 200. In some embodiments, the system may further include a stereotactic surgical system including a patient table, an arc system, CT-accessories for neuro imaging, and/or MR accessories for neuro imaging. The arc system may be any arc system that enables and provides target coordinates on the patient to assist in precision surgery.

As described above, a surgeon can use the above described immersive distraction apparatus 100 to place the patient in a more relaxed state during surgery by creating an immersive distraction therapy such as a virtual reality. In at least one instance, the immersive distraction therapy can include a device used to display games, movies, or other 3D experiences using, for example, the Google VR software package. While Google VR software is described herein, it should be fully understood that any other virtual reality software can be used in connection with the immersive distraction apparatus 100 described herein. While the above description indicates the immersive distraction apparatus 100 is created for use with a standard head frame 200 it should be readily understood that the immersive distraction apparatus can be designed as add-ons for specific surgical head frames. Such customized immersive distraction apparatus can have the structure altered as necessary to be used with various medical equipment used around the world.

The immersive distraction therapies described herein can include visual, as well as audible, stimulation for a patient. As described above, some neurosurgeries require a surgeon to interact with the patient to ensure no damage is done to healthy portions of the brain. For example, software can be used to create specialized experiences which are beneficial during different procedures including, but not limited to, entertainment, stimulation of certain areas of the brain, and dexterity analysis. In at least one instance, where the risk of damage is low the immersive distraction therapy can provide video entertainment to calm the patient. In another instance, where the risk of damage to certain areas is high the immersive distraction therapy can provide stimulation to certain parts of the brain which a surgeon can monitor. In yet another instance, the immersive distraction therapy can include instructions for the patient to perform certain tasks including, but not limited to, movement (including phalange and eye movement), speech, or any other tasks that would assist the surgical team in analyzing proper brain function. Such software experiences can additionally allow the immersive distraction apparatus to be used to assist in neuroscience research. In some instances, the software experience can be controlled via patient motion such as via a controller.

The device can also include an auditory component. The distraction component of the device includes Bluetooth, wired, wifi, or other known connectivity to the virtual reality system, which aids to minimize environmental noise. In an exemplary embodiment the apparatus includes a bone anchored conduction of sound to enhance the distraction experience. In some embodiments, the apparatus uses the frame connector vibratory tactile stimuli which aids to enhance distraction.

Having described several embodiments, it will be recognized by those skilled in the art that various modifications, alternative constructions, and equivalents may be used without departing from the spirit of the disclosure. Additionally, a number of well-known processes and elements have not been described in order to avoid unnecessarily obscuring the present disclosure. Accordingly, the above description should not be taken as limiting the scope of the disclosure.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An immersive distraction apparatus comprising:
   an attachment portion comprising an engagement element and a front plate; and
   a base portion coupled with the attachment portion, the base portion comprising a top panel and a display aperture formed between a viewing frame and a back plate, the top panel having a slot formed therein to retain the engagement element of the attachment portion; and
   one or more frame connectors operable to attach the immersive distraction apparatus to a head frame,
   wherein the one or more frame connectors include vibratory tactile stimuli.

2. The immersive distraction apparatus of claim 1, wherein the viewing frame further includes an opening providing access to the display aperture.

3. The immersive distraction apparatus of claim 2, wherein the display aperture is sized to fit a device therein.

4. The immersive distraction apparatus of claim 2, wherein the front plate of the attachment portion further includes two cut outs spaced apart, each of the two cut outs sized to fit a lens therein.

5. The immersive distraction apparatus of claim 4, further comprising two lenses coupled with the two cut outs of the attachment portion.

6. The immersive distraction apparatus of claim 5, wherein the viewing frame further includes one or more receiving apertures capable of receiving a connector of the one or more frame connectors.

7. The immersive distraction apparatus of claim 6, wherein the connector has a first protrusion sized to fit in the one or more receiving apertures of the viewing frame and a second protrusion sized to mount with the head frame.

8. The immersive distraction apparatus of claim 1, wherein the apparatus includes an auditory component.

9. The immersive distraction apparatus of claim 1, wherein the apparatus provides bone anchored conduction of sound.

10. An immersive distraction therapy system comprising:
    an immersive distraction apparatus comprising:
       an attachment portion comprising an engagement element and a front plate; and
       a base portion coupled with the attachment portion, the base portion comprising a top panel and a display aperture formed between a viewing frame and a back plate, the top panel having a slot formed therein to retain the engagement element of the attachment portion;
    a head frame comprising:
       at least two supports, wherein the immersive distraction apparatus is mounted to the at least two supports; and
    one or more frame connectors operable to attach the immersive distraction apparatus to the head frame,
    wherein the one or more frame connectors include vibratory tactile stimuli.

11. The immersive distraction system of claim 10, further comprising a patient table.

12. The immersive distraction system of claim 10, further comprising an arc system attached to a patient table to provide locations of target coordinates.

13. The immersive distraction system of claim 10, further comprising one or more MR accessories.

14. The immersive distraction system of claim 10, further comprising one or more CT accessories.

* * * * *